(12) United States Patent
Vannas

(10) Patent No.: US 9,664,622 B2
(45) Date of Patent: May 30, 2017

(54) SPARK SENSING DEVICE WITH OPTICAL ELEMENT

(71) Applicant: ATEXON OY, Oulunsalo (FI)

(72) Inventor: Mika Vannas, Tyrnävä (FI)

(73) Assignee: ATEXON OY, Oulunsalo (FI)

( * ) Notice: Subject to any disclaimer, the term of this patent is extended or adjusted under 35 U.S.C. 154(b) by 214 days.

(21) Appl. No.: 14/558,417

(22) Filed: Dec. 2, 2014

(65) Prior Publication Data

US 2015/0153285 A1   Jun. 4, 2015

(30) Foreign Application Priority Data

Dec. 3, 2013   (EP) ..................................... 13195408

(51) Int. Cl.
| | | |
|---|---|---|
| *G01N 21/67* | (2006.01) | |
| *G01J 5/00* | (2006.01) | |
| *G08B 17/12* | (2006.01) | |
| *G01J 5/08* | (2006.01) | |
| *G01J 5/04* | (2006.01) | |

(52) U.S. Cl.
CPC ............. *G01N 21/67* (2013.01); *G01J 5/0014* (2013.01); *G01J 5/043* (2013.01); *G01J 5/0806* (2013.01); *G01J 5/089* (2013.01); *G01J 5/0818* (2013.01); *G08B 17/12* (2013.01); *G01N 2201/0806* (2013.01)

(58) Field of Classification Search
CPC ............. G02B 6/00; G02B 6/14; G08B 17/12
USPC ............................................. 250/227.11, 554
See application file for complete search history.

(56) References Cited

U.S. PATENT DOCUMENTS

| | | |
|---|---|---|
| 3,824,392 A | 7/1974 | Tibbling |
| 4,855,718 A * | 8/1989 | Cholin .................... F23N 5/082 250/554 |
| 5,061,026 A * | 10/1991 | Clarke ...................... G01J 1/04 385/147 |
| 7,026,619 B2 | 4/2006 | Cranford |
| 2002/0134138 A1 | 9/2002 | Philipp et al. |

FOREIGN PATENT DOCUMENTS

| | | |
|---|---|---|
| DE | 29 16 086 A1 | 10/1980 |
| SU | 1 729 528 A1 | 4/1992 |
| WO | WO 00/39769 A1 | 7/2000 |

* cited by examiner

*Primary Examiner* — Seung C Sohn

(74) *Attorney, Agent, or Firm* — Birch, Stewart, Kolasch & Birch, LLP

(57) ABSTRACT

The invention relates to the detection of sparks in a channel where material flows. A spark sensing device is positioned in connection with channel where material flows in a flowing direction. The spark sensing device comprises a sensor element and an optical element that transfers a radiation of a spark to the sensor element. The optical element is made of optically transparent material. The optical element is such that it shapes the collection beam of the sensor element to be asymmetrical whereby the viewing angle of the sensor element is wider in a direction transverse to the flowing direction than in the flowing direction.

14 Claims, 4 Drawing Sheets

Angle in degrees

SPARK SENSING DEVICE WITH OPTICAL ELEMENT

FIELD OF THE INVENTION

The invention relates to detection of sparks in a channel where material flows.

BACKGROUND OF THE INVENTION

Solutions for detecting sparks in a channel are disclosed in documents WO 00/39769, U.S. Pat. Nos. 5,061,026 and 7,026,619, for example. One of the main problems of the existing spark detection systems is that in order to effectively see the sparks over the whole cross section of a channel, at least two devices need to be used. Typically two devices are placed opposite to each other so that they both together can see the whole cross section. If only one device is used, sparks from the whole cross section of the pipe cannot be detected. Another problem is that detection sensitivity variations are large within the sensitivity range. In particular, the detection sensitivity goes near to zero at angles +90° and −90°. Spark detection systems are typically used in applications such as fire extinguishing systems whereby it is very important that the sensitivity is good and uniform across the whole cross section of the channel. Another typical disadvantage is also that the device penetrates too much into the channel and thereby the device is at risk of damage because of the material flow. If a protective housing of the device is made of optically transparent material the durability of the housing is poor. Sensor elements are also exposed to electromagnetic interference, which reduces the sensitivity of the device. If the dimensions of the spark sensing device are large problems concerning attaching the device and vibration resistance arise.

BRIEF DESCRIPTION OF THE EMBODIMENTS

An object of the invention is to provide a new spark sensing device and a new method for spark sensing.

The features of the invention are disclosed in the independent claims. Embodiments of the invention are disclosed in the dependent claims.

In a solution a spark sensing device is positioned in connection with a channel where material flows in a flowing direction. The spark sensing device comprises a sensor element and an optical element that transfers a radiation of a spark to the sensor element. The optical element is made of optically transparent material. The optical element is such that it shapes the collection beam of the sensor element to be asymmetrical whereby the viewing angle of the sensor element is wider in a direction transverse to the flowing direction than in the flowing direction. The overall response of such a sensing device is extremely good. It is also possible to achieve a very uniform response across the full angular range of the collection beam though only one sensor element needs to be used. It is possible to detect substantially the whole cross sectional area of the channel using only one sensing device. The overall costs of the solution are also reasonable because of the need of only one sensor and due to small amount of required optical components and their relatively small size.

In an embodiment the optical element shapes the collection beam such that the viewing angle of the sensor element is wider than 160°, preferably wider than 180°, in a direction transverse to the flowing direction. In an embodiment the optical element shapes the collection beam such that the viewing angle of the sensor element is narrower than 140°, preferably narrower than 90°, in the flowing direction.

According to an embodiment the optical element may be in the form of a lens or a light guide or a combination thereof. In another embodiment the penetration of the optical element in to the channel is less than half of the largest dimension of the optical element in a direction transverse to the penetration direction of the optical element. Such a sensing device is durable against breakage caused by the material flowing in the channel.

In another embodiment the spark sensing device may also comprise a protecting structure on a side of the optical element. The height of the protecting structure may be at least as high as the penetration of the optical element in to the channel. Such a spark sensing device is extremely well protected against breakage caused by the material flowing in the channel.

The spark sensing device may comprise an optical rod between the optical element and the sensor element. The optical rod transfers the radiation from the optical element to the sensor element. Such a solution has excellent electromagnetic compatibility properties. Furthermore, high temperatures in the channel, for example, do not harm the sensitive electronics in the sensor element.

In this connection the term spark comprises embers, hot particles, bright sparks, etc.

BRIEF DESCRIPTION OF THE DRAWINGS

In the following the invention will be described in greater detail by means of preferred embodiments with reference to the accompanying drawings, in which FIG. 1 schematically shows a spark detection and extinguishing system, FIG. 2 schematically shows an enlarged side view of a spark sensing device shown in FIG. 1.

DETAILED DESCRIPTION OF THE INVENTION

Figure 1:
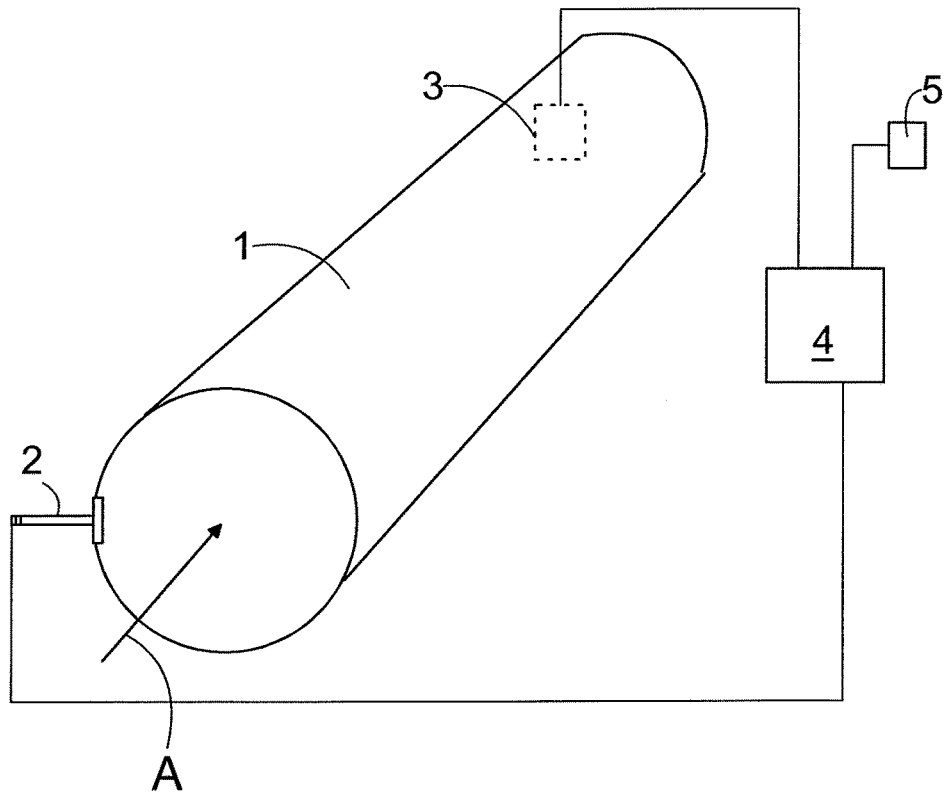

FIG. 1 schematically shows a part of a channel 1 where material flows. The channel 1 may be a pipe or duct, for example. The channel 1 may be used for transferring the material. The material flowing in the channel may be saw dust, wood chips, pulp, pellets, metal chips, dust or any other suitable material. The material may be combustible.

The cross section of the channel 1 may be round, oval or polygonal, for example. The diameter of the channel may be in the range of 0.05 m to several meters, for example.

The material may be transferred in the channel 1 by means of air, for example. In such case the channel 1 thereby comprises a mixture of air and the transferred material.

Mechanical transfer means, such as a screw, may also be used for transferring the material such that the material flows in a flowing direction. The flowing direction is denoted with arrow A in the Figures. Possible sparks in the channel need to be detected.

FIG. 1 shows a spark sensing device 2 positioned in connection with the channel 1. The system shown in FIG. 1 also comprises an extinguishing unit 3. The extinguishing unit 3 is positioned downstream the spark sensing device 2.

The spark sensing device 2 and the extinguishing unit 3 are connected to a control unit 4. The control unit 4 may control the operation of the entire system. When the spark sensing device 2 detects a spark the control unit 4 activates the extinguishing unit 3 to extinguish the detected sparks. The extinguishing unit 3 may spray water mist, for example, to extinguish the detected sparks.

The system may also comprise a signaling device 5. The signaling device 5 may give an audible and visible alarm when necessary.

The system may also comprise temperature sensing means connected to the control unit 4 and arranged to detect the overheating of electric devices, for example. The control unit 4 may report alarms, line falls and overheating of electric motors, for example. The control unit 4 may switch electricity off of the heated device thus preventing a fire from kindling.

Figure 2:
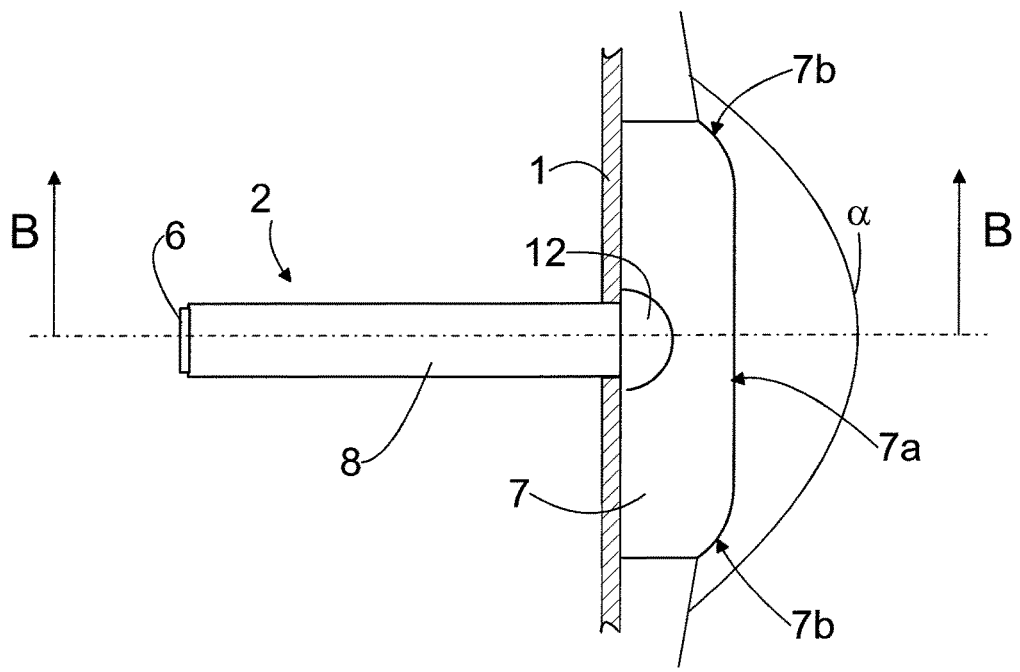
Figure 4:
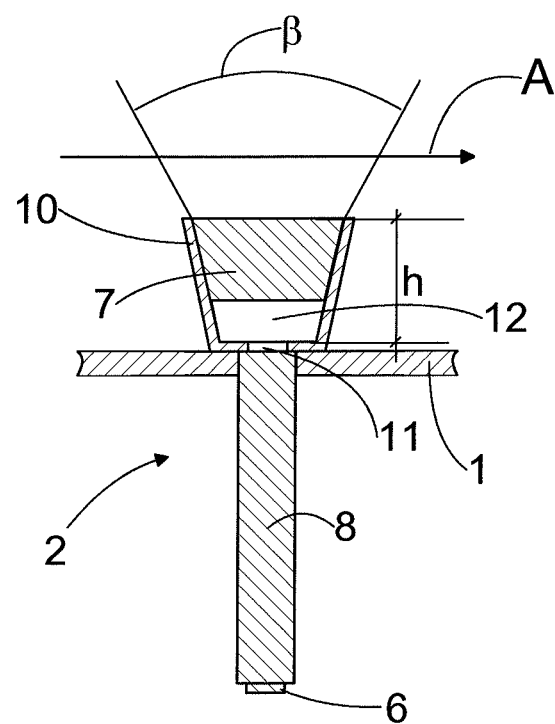
FIG. 4 is a schematic cross-sectional view along line B-B in FIG. 2.

FIG. 2 shows the spark sensing device 2 in a plane transverse to the flowing direction, i.e. in the cross-sectional plane of the channel. FIG. 4 shows the spark sensing device 2 in a cross-sectional plane along line B-B in FIG. 2.

The spark sensing device 2 comprises a sensor element 6 and an optical element 7. The optical element 7 transfers a radiation of a spark to the sensor element 6. The spark sensing device 2 needs only comprise the sensor element 6 and the optical element 7 but in the embodiment shown in FIG. 2 the spark sensing device 2 also comprises a light pipe, such as an optical rod 8, between the optical element 7 and the sensor element 6. The sensor element 6 may be a photodiode detector or another light sensitive element, for example.

In the embodiment shown in FIG. 2 only the optical element 7 is positioned inside the channel 1. At least most of the other parts of the spark sensing device 2, such as the optical rod 8 and the sensor element 6, are at least mainly positioned outside of the channel 1.

The optical element 7 shapes the collection beam of the sensor element to be asymmetrical. A collection beam may also be called a detection beam. In the plane perpendicular to the flowing direction the collection beam covers the whole cross-section of the channel. In the plane parallel to the flowing direction the collection beam is narrower. As shown in FIGS. 2 and 4 the viewing angle α of the sensor element is wider than 160° in a direction transverse to the flowing direction A and the viewing angle β is narrower than 140° in the flowing direction A.

Figure 7:
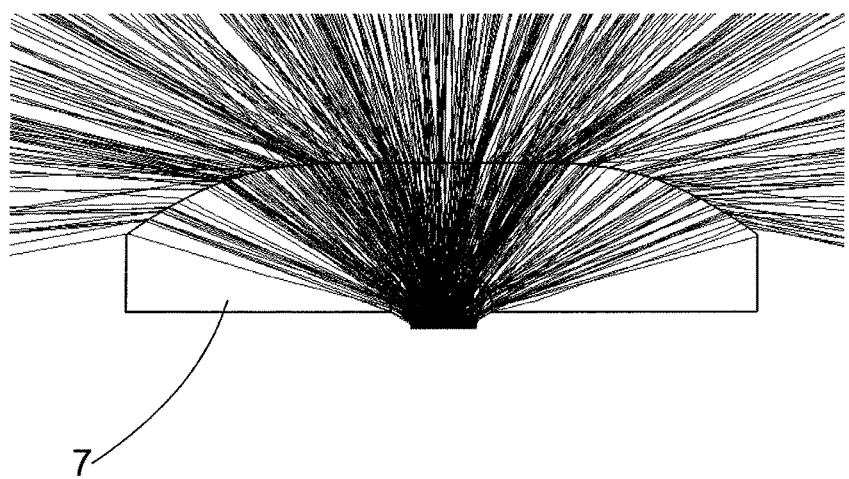
FIG. 7 is a schematic cross-section, transverse to the flow direction, of an optical element with some simulated rays.
Figure 8:
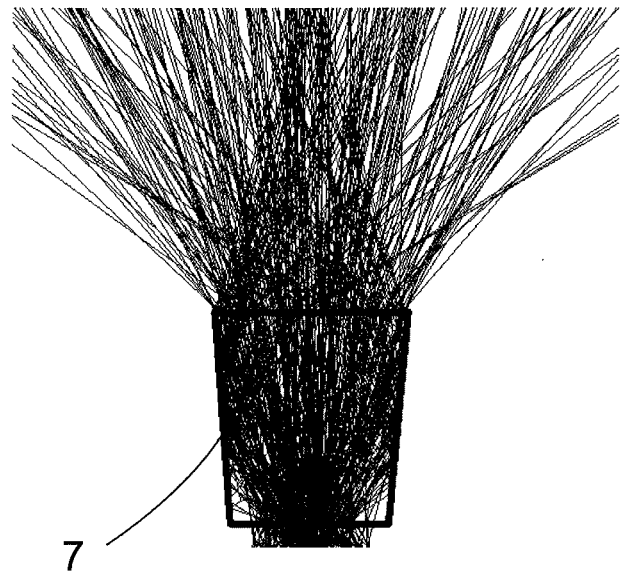
FIG. 8 is a schematic cross-section, in a plane parallel to the flow direction, of an optical element with some simulated rays

FIGS. 7 and 8 show schematic cross sections of an embodiment of the invention together with some simulated rays which demonstrate the collection beam. Naturally, in reality the number of rays is much higher whereby the detection area is continuously covered by the device. FIG. 7 shows that the viewing angle of the sensor element is wider than 180° in a direction transverse to the flowing direction A. FIG. 8 shows that the viewing angle is less than 90° in the flowing direction.

The optical element 7 may be in the form of a lens or in the form of a light pipe or in the form of a light guide or the optical element 7 may be a combination of a lens and a light guide.

One solution for providing an asymmetrical collection beam without an optical element is to cover a sensor element by an aperture element that includes a slot or a plurality of mutually adjacent slots that are orientated in a direction transverse to the flowing direction A. An optical element shaping the collection beam, however, provides a much higher overall response of the detected radiation to the sensor element than a sensing device where the collection beam has been shaped asymmetrical without using an optical element. In the embodiment where the optical element is used a very uniform response is also achieved even though only one sensor element 6 needs to be used in connection with the spark sensing device 2. It is possible to detect substantially the whole cross sectional area of the channel 1 using only one spark sensing device 2 on a certain wavelength range.

When the collection beam is shaped asymmetrical by the optical element such that the viewing angle in the flowing direction is made narrower, the collection beam in the direction transverse to the flowing direction A is wide and still the intensity is high and the uniformity of the collection beam is excellent. When the collection beam is uniform the signal strength is uniform regardless of the detecting direction. This provides reliable measurement of the energy level of the detected particle. If the uniformity would be substantially different on the edge portions of the collection beam, for example, a similar spark would cause a different signal depending on the detection angle.

Narrowing of the viewing angle β in the flowing direction A also provides that the particles to be detected are on the detecting area for a shorter period of time. Thus the signal frequency becomes higher and therefore the sparks are more easily separated from the noise. Furthermore, the overall sensitivity can be increased because the available optical etendue of the detector can be filled from a smaller angular detection range.

Figure 9:
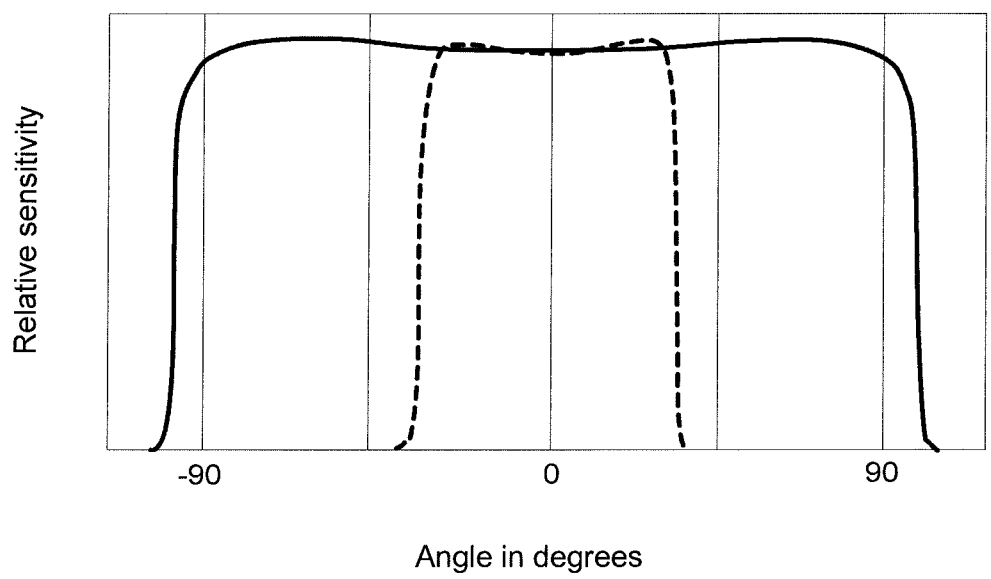
FIG. 9 is an example of the angular sensitivity of a spark sensing device.

As shown in FIG. 2 the cross-section on the optical element is the same as an aspheric cylinder lens in the direction transverse to the flowing direction A. This form widens the collection beam such that the response is substantially uniform across an angle that is substantially 180° or over 180° as shown in FIG. 9. The angle may be designed to be smaller if the channel geometry allows using a smaller angular detection range. The operation of the aspheric lens form is shown also in FIG. 7. In FIG. 7 the operation is illustrated by the simulated ray paths.

As shown in the FIG. 4 the optical element 7 is in the flowing direction an opening tapered light pipe that shapes the viewing angle β to be in the flowing direction A substantially smaller than in the direction transverse to the flowing direction A. The viewing angle may be less than 140°, preferably less than 90°. In the embodiment shown in FIG. 4 the viewing angle is about 60°. The operation of the tapered light pipe form is shown in FIG. 8. In FIG. 8 the operation is illustrated by the simulated ray paths.

In the embodiment shown in FIG. 2 the cross-section of the optical element 7 has a middle portion 7a and two end portions 7b. The middle portion 7a is flat and the end portions 7b are rounded or curved. The optical element 7 may also be formed such that instead of being flat the middle portion 7a is concave or convex. The end portions 7b may also have a form different than shown in FIG. 2. The size and shape of the optical element 7 may differ based on an optimization taking in to account features, such as effectiveness, viewing angle, uniformity and the type of the sensor element used, that are wanted to be emphasized.

Figure 3:
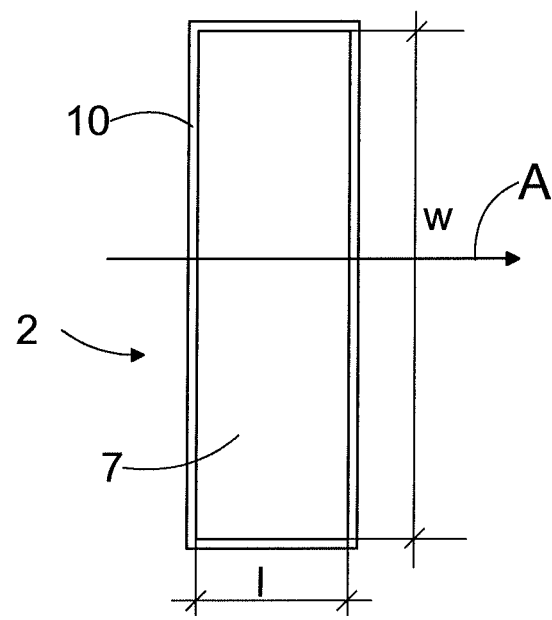
FIG. 3 is schematic front view of a spark sensing device shown in FIG. 2.

In the embodiment shown in the Figures the optical element 7 does not have a rotationally symmetrical shape. In the embodiment shown in the Figures the optical element 7 has a shape of a rectangle seen in a front view. Especially FIG. 3 shows this feature. The optical element 7 may also have an oval, elliptical, polygonal or any other rotationally asymmetrical shape in a front view. The optical element 7 may have also have a rotationally symmetrical shape in a front view if it, however, acts optically asymmetrically.

The optical element 7 may also be a biconic aspheric lens. Furthermore, the optical element 7 may be an asymmetrical light guide, for example, such as an asymmetrical tapered light pipe. The optical element 7 may also be a branched light guide. The optical element 7 may also be any combination of a lens, a symmetrical light guide, an asymmetrical light guide and a branched light guide. In an embodiment the optical element 7 comprises only one element side by side for shaping the collection beam to be asymmetrical. In such a solution the beam is continuous close to the element also.

The width w of the optical element 7 is larger than the length l of the optical element 7. In the embodiment of the Figures the height h of the optical element 7 is smaller than half of the width w of the optical element 7. Thus, in this embodiment the optical element 7 is rather low whereby the penetration of the optical element 7 in to the channel 1 is rather small and therefore the material flowing in the channel 1 does not easily hit the optical element. Thus, the material does not easily break the optical element 7. The width w of the optical element 7 may be in the range of 5 to 50 mm, or in the range of 15 to 30 mm, for example. The length l of the optical element 7 may be in the range of 2 to 15 mm, for example. The height of the optical element 7 may be in the range of 2 to 20 mm, for example. These given values are not, however, restricting the possible sizes of the optical element. Depending on the application where the device is installed and depending on the sensor element used and other targeted properties the same invention can be implemented in whatever size is found feasible.

As shown in FIGS. 3 and 4 the spark sensing device 2 may also comprise a protecting structure 10. The protecting structure 10 extends on the sides of the optical element 7. The object of the protecting structure 10 is to mechanically protect the optical element 7 through which the radiation energy is transferred to the sensor element 6.

The height of the protecting structure 10 may be at least as high as the penetration of the optical element 7 in to the channel 1. The protecting structure 10 may be of metal or plastic, for example. An optical element 7 protected by the protecting structure 10 is extremely well protected against breakage caused by the material flowing in the channel 1.

The protecting structure 10 forms a so called protection by enclosures whereby the optical element withstands high impact energy. Thus, the protection structure 10 makes it possible to use the device in an explosive atmosphere even though the device comprises optical parts.

The protecting structure 10 may extend below the optical element 7. In such case the protecting structure 10 is provided with a hole 11 through which the radiation passes to the sensor element 6. If the protecting structure 10 is of metal, for example, the device has excellent electromagnetic compatibility properties.

The lower surface of the optical element 7 is provided with a notch 12. The hole 11 is positioned by the notch. The optical rod 8 is positioned such that its first end is positioned on the hole 11 and its second end is by the sensor element 6. Thus, the radiation passes through the optical element 7 and the hole 11 and further via the optical rod 8 to the sensor element 6. The end of the optical rod 8 is positioned such that the rod 8 transfers the radiation collected by the optical element 7 to the sensor element 6.

The lower surface of the optical element 7 may have different forms or shapes. Thus, the shape of the notch 12 may differ from the shape shown in the Figures, for example. Furthermore, in an embodiment the lower surface of the optical element 7 does not have a notch at all.

The optical element 7 and the optical rod 8 are made of optically transparent material for the used wavelength range and which material has suitable optical and mechanical properties. Examples of the material for the optical element 7 and for the optical rod 8 are glass, plastic, quartz glass and silicate.

The optical rod 8 may be such that its cross section is a square. The cross section of the optical rod 8 may also be round, oval or elliptical, for example. The cross section of the optical rod 8 may also have a shape of a hexagon or any other polygon, for example. The optical rod 8 may also be a hollow light guide having a reflective inner surface or an optical fiber or a bundle of optical fibers.

Figure 5:
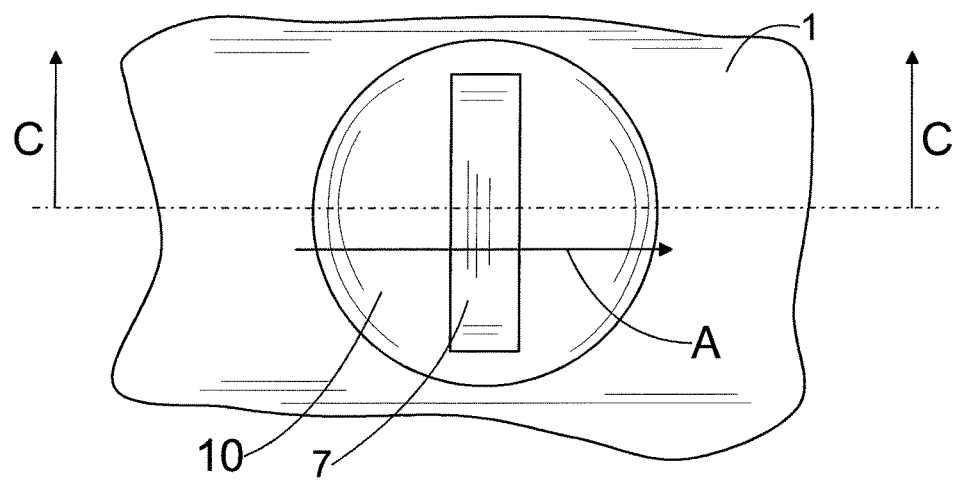
FIG. 5 is a schematic front view of another spark sensing device.
Figure 6:
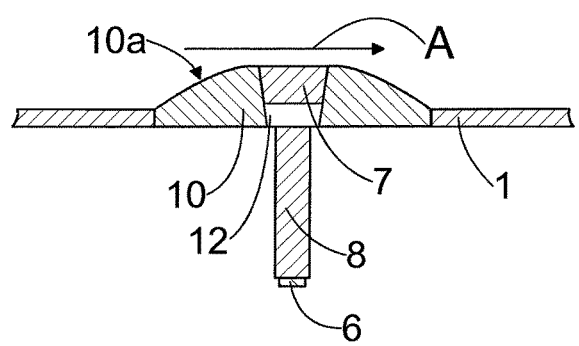
FIG. 6 is a schematic cross-sectional view along line C-C in FIG. 5.

In the embodiment described in FIGS. 5 and 6 the protecting structure 10 has an overall shape of a flat dome. The optical element 7 is positioned in to a groove in the dome shaped protecting structure 10. As shown in FIG. 6 the protecting structure 10 has a slanting or curved surface 10a. Because of the surface 10a the material particles flowing in the channel are guided such that they do not hit the optical element 7. The shape of the protecting structure also provides that the spark sensing device does not essentially affect the flow of the material in the channel 1.

The spark sensing device 2 is positioned in connection with the channel such that a hole the size of which corresponds to the size of the protecting structure 10 is formed to the wall of the channel. Thereby the optical element 7 and the protecting structure 10 may be assembled in place outside of the channel 1. Also the penetration of the spark sensing device into the channel is minimal.

In the system described in FIG. 1 it is possible to use only one spark sensing device. However, it is possible to use in the system two or more spark sensing devices. In the case that two or more spark sensing devices are used their sensor elements may be similar or different. If the sensor elements 6 are different one of the sensor elements may detect radiation on a certain first wavelength range and the other sensor element may detect radiation on a second wavelength range. If the spark sensing devices detect radiation on different wavelength ranges it is possible to detect radiation across the full cross sectional area of the channel on an extremely wide wavelength range.

If two or more spark sensing devices are used they can be positioned on the opposite sides of the channel 1. The spark sensing devices may be on the same position in the flowing direction A. The spark sensing devices may also be one after the other in the flowing direction A. Due to the large angular view of the device according to the invention, it is also possible to position the spark sensing devices on the same side of the channel 1.

If different spark sensing devices have sensor elements detecting different wavelength ranges different kind of sparks are detected effectively. Sparks having different temperatures radiate on a different wavelength. A cooler spark radiates on a longer wavelength than a hotter spark whereby by using several different sensor elements all kind of ignition sources are effectively detected.

It will be obvious to a person skilled in the art that, as technology advances, the inventive concept can be implemented in various ways. The invention and its embodiments are not limited to the examples described above but may vary within the scope of the claims.

The spark sensing device may also comprise, instead of only one sensor element 6, two or more sensor elements side by side. One sensor element may also comprise photo diodes which are sensitive to different wavelengths. It is also possible to use several separate sensor elements where the radiation is transferred from the optical element or from the end of the optical rod by a branching bundle of fibres or by using light guides or by using any suitable means. Also when only one sensor element is used the sensor element can be positioned farther away and transfer the radiation along a fibre or a light guide from the optical element or from the end of the optical rod to the sensor element.

It is also possible to integrate the optical element and the optical rod such that they are integrated into the same component.

It is possible to achieve a uniform response both in the direction transverse to the flowing direction and in the flowing direction. If needed, however, the response in the flowing direction, for example, may be arranged to be uneven.

The invention claimed is:

1. A spark sensing device to be positioned in connection with a channel where material flows in a flowing direction, the spark sensing device comprising:
    a sensor element; and
    an optical element that transfers a radiation of a spark to the sensor element,
    wherein the optical element is made of optically transparent material and the optical element is such that it shapes a collection beam of the sensor element to be continuous near the optical element and to be asymmetrical, whereby a viewing angle of the sensor element is wider in a direction transverse to the flowing direction than in the flowing direction.

2. A spark sensing device as claimed in claim 1, wherein the optical element is a lens or a combination of a lens and a light guide.

3. A spark sensing device as claimed in claim 2, wherein the optical element operates as an aspheric lens in the direction transverse to the flowing direction.

4. A spark sensing device as claimed in claim 3, wherein the optical element operates as a light pipe in a plane parallel to the flowing direction.

5. A spark sensing device as claimed in claim 1, wherein a penetration of the optical element to the channel is less than half of a largest dimension of the optical element in a direction transverse to the penetration direction of the optical element.

6. A spark sensing device as claimed in claim 1, wherein the spark sensing device comprises a protecting structure on a side of the optical element.

7. A spark sensing device as claimed in claim 6, wherein a height of the protecting structure is at least as high as the penetration of the optical element in to the channel.

8. A spark sensing device as claimed in claim 6, wherein the protecting structure has an overall shape of a flat dome.

9. A spark sensing device as claimed in claim 1, wherein the spark sensing device comprises a light pipe between the optical element and the sensor element.

10. A spark sensing device as claimed in claim 1, wherein the optical element shapes the collection beam such that the viewing angle of the sensor element is wider than 160°, preferably wider than 180°, in a direction transverse to the flowing direction.

11. A spark sensing device as claimed in claim 1, wherein the optical element shapes the collection beam such that the viewing angle of the sensor element is narrower than 140°, preferably narrower than 90°, in the flowing direction.

12. A spark sensing device as claimed in claim 1, wherein the optical element shapes the collection beam such that the viewing angle of the sensor element covers substantially the whole cross sectional area of the channel.

13. A spark detection and extinguishing system comprising at least one spark sensing device according to claim 1.

14. A method for detecting sparks in a channel where material flows in a flowing direction, the method comprising:
    detecting sparks on a certain first wavelength range with a spark sensing device, the spark sensing device comprising a sensor element and an optical element that transfers a radiation of a spark to the sensor element, the optical element being made of optically transparent material and wherein the step of detecting sparks comprises shaping, via the optical element, a collection beam of the sensor element to be asymmetrical such that a viewing angle of the sensor element is wider in a direction transverse to the flowing direction than in the flowing direction, across substantially a whole cross sectional area of the channel using on said certain first wavelength range only one spark sensing device; and
    using said one spark sensing device for detecting the sparks on said certain first wavelength range and another spark sensing device for detecting on a second wavelength range, whereby said first and second wavelength ranges are detected by using only two spark sensing devices.

* * * * *